(12) United States Patent
Smith et al.

(10) Patent No.: US 7,659,107 B2
(45) Date of Patent: Feb. 9, 2010

(54) RAPID TEST FOR GLYCATED ALBUMIN

(75) Inventors: Henry J. Smith, San Jacinto, CA (US); Asad Zaidi, Cerritos, CA (US)

(73) Assignee: Epinex Diagnostics, Inc., Tustin, CA (US)

( * ) Notice: Subject to any disclaimer, the term of this patent is extended or adjusted under 35 U.S.C. 154(b) by 366 days.

(21) Appl. No.: 10/538,392

(22) PCT Filed: Sep. 22, 2004

(86) PCT No.: PCT/US2004/031202

§ 371 (c)(1),
(2), (4) Date: Apr. 27, 2006

(87) PCT Pub. No.: WO2005/031356

PCT Pub. Date: Apr. 7, 2005

(65) Prior Publication Data

US 2006/0223192 A1 Oct. 5, 2006

Related U.S. Application Data

(60) Provisional application No. 60/505,392, filed on Sep. 23, 2003.

(51) Int. Cl.
G01N 33/543 (2006.01)
G01N 33/553 (2006.01)
G01N 33/558 (2006.01)
G01N 33/546 (2006.01)

(52) U.S. Cl. .................. 435/287.2; 422/56; 422/57; 422/58; 422/61; 435/287.7; 435/287.9; 435/805; 435/810; 435/970; 435/973; 435/975; 436/164; 436/169; 436/514; 436/518; 436/524; 436/525; 436/531; 436/533; 436/534; 436/807; 436/808; 436/810; 436/815

(58) Field of Classification Search .............. None
See application file for complete search history.

(56) References Cited

U.S. PATENT DOCUMENTS 4,879,039 A 11/1989 Takahashi et al.
5,004,546 A 4/1991 Takahashi et al.

(Continued)

FOREIGN PATENT DOCUMENTS

EP 0724157 7/1996

(Continued)

OTHER PUBLICATIONS

A1c NOWProduct Insert, Metrika, (No date available).

*Primary Examiner*—Christopher L Chin
(74) *Attorney, Agent, or Firm*—Louis C. Cullman; Michelle S. Glasky; K&L Gates LLP (57) ABSTRACT

A rapid immunochromatographic assay system is provided for measuring the amount of glycated albumin in a blood sample relative to the total level of albumin in the sample. The assay system is comprised of a disposable cassette that contains the test strips and testing reagents, and a measurement device that automatically reads, calculates and displays the test results over a period of time. The test cassette contains two test strips that are used to measure glycated albumin and total albumin respectively. The strips are contiguous beneath the single sample application well so that the same sample is tested simultaneously by both test strips. Part of the sample will migrate thru the glycated albumin test strip where it will react with the glycated albumin test reagents to yield a glycated albumin result, while part of the sample will migrate thru the total albumin test strip where it will react with the total albumin test reagents to yield a total albumin result. The test cassette is placed within a measuring device such as a reflectance spectrometer or fluorometer, that reads, calculates and expresses the result as the percentage of glycated albumin relative to total albumin in the sample. The results of successive testing that are performed over a period of time are stored in the instrument's memory and displayed in a numerical or graphical format so that the individual's glycated albumin levels can be monitored over time.

16 Claims, 5 Drawing Sheets

Test Strips: Overhead View

U.S. PATENT DOCUMENTS

| | | | |
|---|---|---|---|
| 5,110,745 A | 5/1992 | Kricka et al. | |
| 5,206,144 A | 4/1993 | Zeuthen et al. | |
| 5,284,777 A | 2/1994 | Rosenthal et al. | |
| 5,470,759 A | 11/1995 | Sugiyama et al. | |
| 5,478,754 A | 12/1995 | Brandt et al. | |
| 5,506,144 A | 4/1996 | Sundrehagen | |
| 5,541,117 A | 7/1996 | Karl et al. | |
| 5,559,041 A * | 9/1996 | Kang et al. | 436/518 |
| 5,589,393 A | 12/1996 | Fiechtner et al. | |
| 5,686,316 A | 11/1997 | Fiechtner et al. | |
| 5,882,935 A | 3/1999 | Hirai et al. | |
| 5,962,336 A | 10/1999 | Sun | |
| 5,981,298 A | 11/1999 | Chudzik et al. | |
| 6,027,907 A | 2/2000 | Shinoki et al. | |
| 6,043,043 A | 3/2000 | Yip | |
| 6,162,645 A | 12/2000 | Lee et al. | |
| 6,248,598 B1 | 6/2001 | Bogema | |
| 6,316,265 B1 | 11/2001 | Lee et al. | |
| 6,562,581 B2 | 5/2003 | Law et al. | |
| 6,670,192 B1 * | 12/2003 | Galen et al. | 422/67 |
| 2002/0164811 A1 | 11/2002 | Hud et al. | |
| 2002/0172992 A1 | 11/2002 | Heller | |
| 2003/0068830 A1 | 4/2003 | McCroskey et al. | |
| 2003/0073243 A1 | 4/2003 | Law et al. | |

FOREIGN PATENT DOCUMENTS

| | | |
|---|---|---|
| EP | 0769697 A1 | 4/1997 |
| WO | WO 95/34815 | 12/1995 |
| WO | WO 96/31619 | 10/1996 |
| WO | WO 2004/042364 | 5/2004 |

* cited by examiner

Figure 1. Test strips and cassette

Figure 2  Test Strips: Overhead View

Figure 3  Test Strip. Side view

Figure. 4. Reflectance Spectrometer

Figure.4b. Fluorometer

Figure 5. Modified strip arrangement and cassette design.

Figure 6. Modified strip arrangement and cassette design

Figure 7. Spectrometer and Test Cassette

RAPID TEST FOR GLYCATED ALBUMIN

RELATED APPLICATIONS

This application claims priority to U.S. provisional patent application Ser. No. 60/505,392 filed Sep. 23, 2003.

FIELD OF THE INVENTION

This invention relates generally to medical devices for measuring levels of glycated albumin in blood from patients with diabetes. More specifically, the present invention uses lateral flow immunochromatography to measure both glycated albumin and total albumin in a single sample. Additionally the present invention provides methods for monitoring levels of glycated albumin in the blood of diabetes patients using a point-of-care assay and medical device.

BACKGROUND OF THE INVENTION

Diabetes mellitus, or diabetes, is a disease characterized by elevated levels of plasma glucose. Uncontrolled hyperglycemia is associated with increased risk of vascular disease including, nephropathy, neuropathy, retinopathy, hypertension, and death. There are two major forms of diabetes: Type 1 diabetes (or insulin-dependent diabetes) and Type 2 diabetes (or non insulin-dependent diabetes). The American Diabetes Association has estimated that approximately 6% of the world population has diabetes.

The goal of diabetic therapy is to maintain a normal level of glucose in the blood. The American Diabetic Association has recommended that diabetics monitor their blood glucose level at least three times a day in order to adjust their insulin dosages and/or their eating habits and exercise regimen. However, glucose tests can only measure a point in time result and do not provide an overall assessment of glycemic control over a period of time. The measurement of glycated albumin has proven to be valuable measure of the effectiveness of glycemic control over the preceding 2-3 weeks. The basis for measuring glycated albumin depends on the nonenzymatic glycosylation of albumin and is directly proportional to the level of glucose in plasma over a period of time. The half-life of albumin in plasma is 2-3 weeks and as glycosylation occurs at a constant rate over time the level of glycated albumin provides a measure of the average blood glucose level over the preceding two to three weeks.

Frequent monitoring of the individual's glycated albumin would provide an accurate assessment of overall effectiveness of glycemic control in the individual.

Current methodology for performing tests for glycated albumin are complex to perform or require expensive instrumentation and are generally performed in laboratories. It would be advantageous to develop a simplified point-of-care assay that could be utilized in a doctor's office or by the patient and there is intensive research to develop such a test.

The present invention describes a simplified point-of-care assay that utilizes disposable test strips and a reusable measuring instrument.

SUMMARY OF THE INVENTION

The present invention is directed to medical devices and methods for monitoring levels of glycated albumin in the blood of diabetes patients using a point-of-care assay and medical device. Specifically, the present invention uses lateral flow immunochromatography to measure both glycated albumin and total albumin in a single sample.

In an embodiment of the present invention, an immunochromatographic system is provided for measuring glycated albumin in a blood sample comprising a first test strip that measures glycated albumin and a second test strip that measures total albumin; and a measurement device that reads, calculates and displays the result as the percentage of glycated albumin compared to total albumin in the sample.

In another embodiment of the present invention, the first test strip is comprised of microparticles coated with a first antibody to glycated albumin and an immobilization agent covalently bound to the membrane strip. The immobilization agent is a second antibody to glycated albumin or phenyl boronic acid.

In alternative embodiments of the present invention the first and second antibodies to glycated albumin are individually monoclonal or polyclonal antibodies. The polyclonal antibodies may be the whole antiserum, the IgG fraction or the purified antibody.

In an embodiment of the present invention, the microparticles of the first test strip are selected from the group consisting of colloidal gold particles, latex particles, polystyrene particles, acrylic particles or other solid phase microparticles. Additionally the size of the microparticles can vary from approximately 5 nm to approximately 50 nm in diameter.

In another embodiment of the present invention, the second test strip is comprised of microparticles coated with a first antibody to albumin and an second antibody to albumin covalently bound to the membrane strip.

In an embodiment of the present invention, the first and second antibodies to albumin are individually monoclonal or polyclonal antibodies. The polyclonal anti-albumin antibodies may be the whole antiserum, the IgG fraction or the purified antibody.

In an embodiment of the present invention, the microparticles of the second test strip are selected from the group consisting of colloidal gold particles, latex particles, polystyrene particles, acrylic particles or other solid phase microparticles. Additionally the size of the microparticles can vary from approximately 5 nm to approximately 50 nm in diameter.

In another embodiment of the present invention the microparticles of either of the first or second test strips can have particle size diameters of 10 nm, 20 nm, 30 nm and 40 nm.

In yet another embodiment of the present invention, the microparticles of either the first or second test strip can either colored or tagged with a fluorescent compound.

In an embodiment of the present invention, the first test strip and the second test strip may be arranged in parallel; or opposite to each other; or at an angle to each other. Additionally the first test strip and the second test strip are enclosed in a rigid cassette.

In an embodiment of the present invention the measurement device is a reflectance spectrometer comprising: a reflectance detector for measuring the glycated albumin test result; a reflectance detector for measuring the glycated albumin control band; a reflectance detector for measuring the total albumin test result; a reflectance detector for measuring the total albumin control band; an internal computer chip for measurement and calculation; a liquid crystal display; an external port to transfer data to an external computer and/or printer; a battery and/or an external power source; and a rigid external case with an aperture for inserting the test cassette.

In an embodiment of the present invention the measurement device is a fluorometer composed comprising: a fluorescence detector for measuring the glycated albumin test result; a fluorescence detector for measuring the glycated albumin control band; a fluorescence detector for measuring the total albumin test result; a fluorescence detector for measuring the total albumin control band; an internal computer chip for measurement and calculation; a liquid crystal display; an external port to transfer data to an external computer and/or printer; a battery and/or an external power source; and a rigid external case with an aperture for inserting the test cassette.

In another embodiment of the present invention the measurement device further comprises an internal memory chip capable of storing one or more than one test result.

In yet another embodiment of the present invention, the measurement device can display one or more than one test result on the measurement device's liquid crystal display in numerical format or in graphical format. Additionally the test results can be transferred to an external computer or printer.

In an embodiment of the present invention, a method of monitoring glycated albumin using a point-of-care assay is provided comprising: depositing a drop of blood into a sample well of an immunochromatography system test cassette; transferring said blood into the sample application pad thereby allowing blood plasma to pass into a first conjugate pad of a first test strip; binding said blood plasma to anti-glycated albumin antibody-coated microparticles in said first conjugate pad; allowing blood plasma-bound anti-glycated albumin antibody-coated microparticles to migrate across said first conjugate pad to a fixed band of membrane-bound anti-glycated albumin antibody; binding said blood plasma-bound anti-glycated albumin antibody-coated microparticles to said membrane bound anti-glycated albumin antibody to form a visible band; inserting said immunochromatography system test casette into a measurement device; and providing numerical results of glycated albumin levels.

In an embodiment of the present invention, the method of monitoring glycated albumin using a point-of-care assay further comprises: depositing a drop of blood into a sample well of an immunochromatography system cassette; transferring said blood into the sample application pad thereby allowing blood plasma to pass into a second conjugate pad of a second test strip; binding said blood plasma to anti-total albumin antibody-coated microparticles in said second first conjugate pad; allowing blood plasma-bound anti-total albumin antibody-coated microparticles to migrate across said second conjugate pad to a fixed band of membrane-bound anti-total albumin antibody; binding said blood plasma-bound anti-total albumin antibody-coated microparticles to said membrane bound anti-total albumin antibody to form a visible band; inserting said immunochromatography system test cassette into a measurement device; and providing numerical results of total albumin levels.

In another embodiment of the present invention, a method of monitoring glycated albumin using a point-of-care assay is provided wherein glycated albumin levels and said total albumin levels are used to determine percent glycated albumin.

DESCRIPTION OF THE INVENTION

This invention utilizes the principle of lateral flow immunochromatography to measure both glycated albumin and total albumin. The patient's blood sample is placed in a test cassette that contains reagents to separate the plasma from the red blood cells and to perform the test. The test cassette is then inserted into a measuring instrument that reads, calculates and reports the result.

Figure 7:
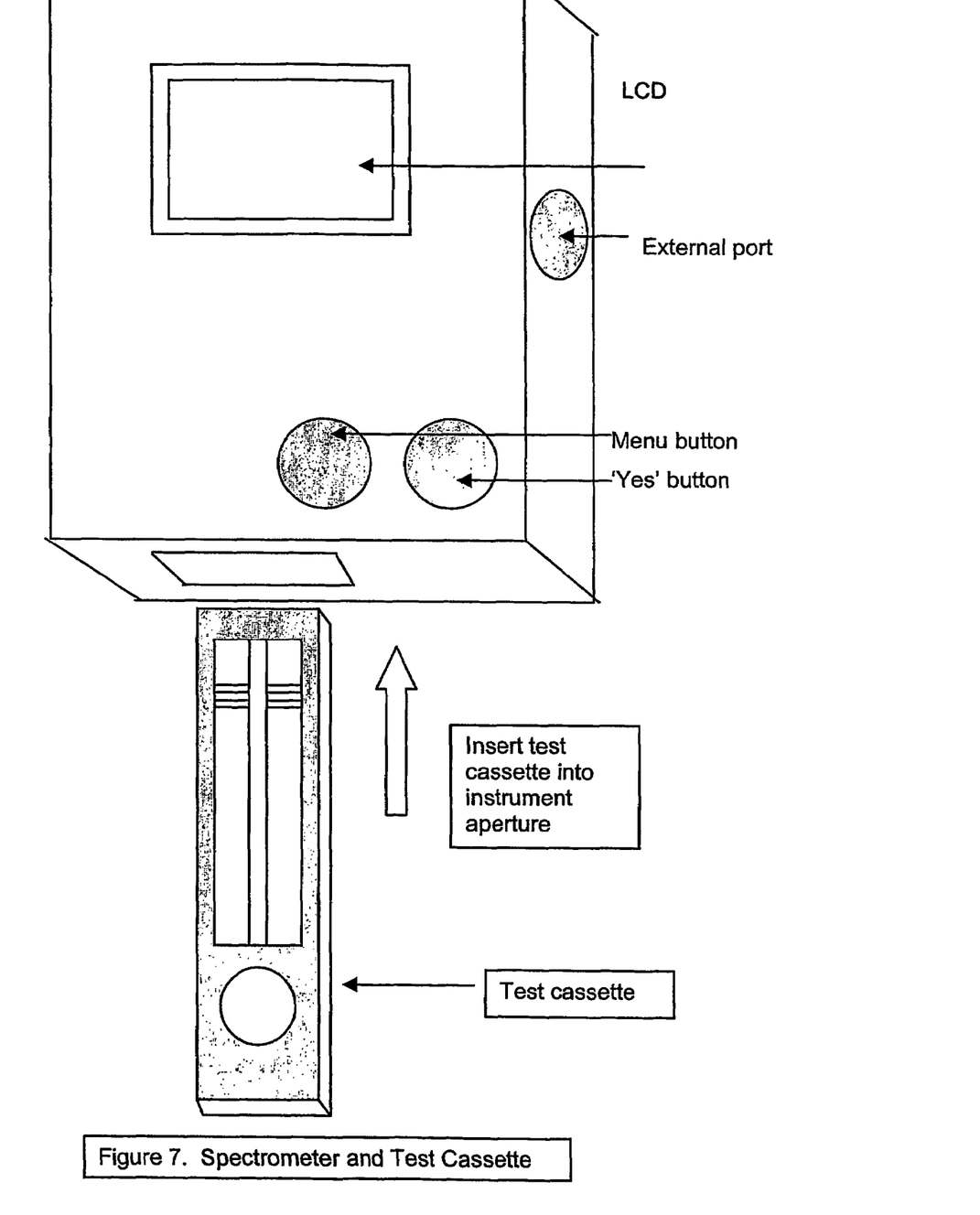
FIG. 7 depicts a reflectance spectrometer and test strip as used in accordance with the methods of the present invention.

The rapid assay for glycated albumin is an immunochromatographic method that utilizes antibodies to glycated albumin and antibodies to total albumin on test strips. In order to measure the percent of glycated albumin to total albumin, two procedures are involved. The first procedure utilizes an immunochromatographic test strip to measure glycated albumin. The second procedure utilizes an immunochromatographic test strip to measure total albumin. Both strips are contained within a single exterior cassette (FIG. 1) that is inserted into a measuring instrument (FIG. 7) that automatically reads, calculates and displays the result.

Glycated Albumin Test

Figure 1:
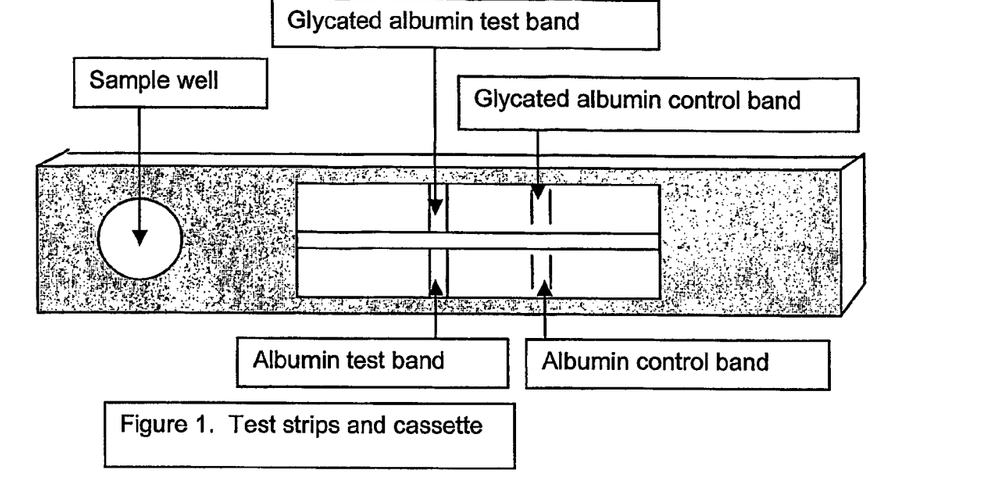
FIG. 1 depicts a first view of the test strips made in accordance with the teachings of the present invention.
Figure 2:
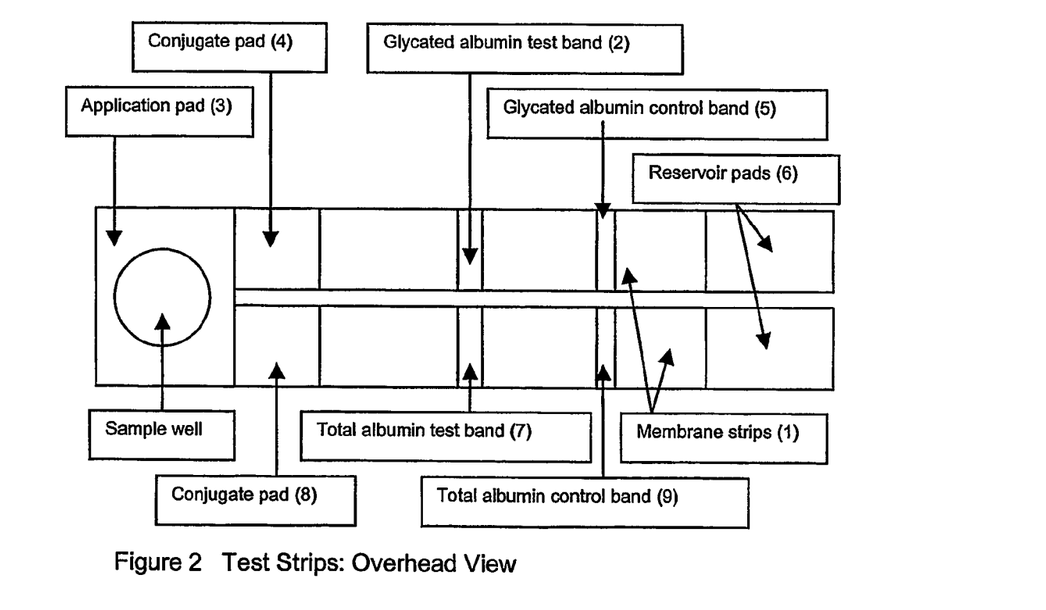
FIG. 2 depicts a second view of the test strips made in accordance with the teachings of the present invention.
Figure 3:
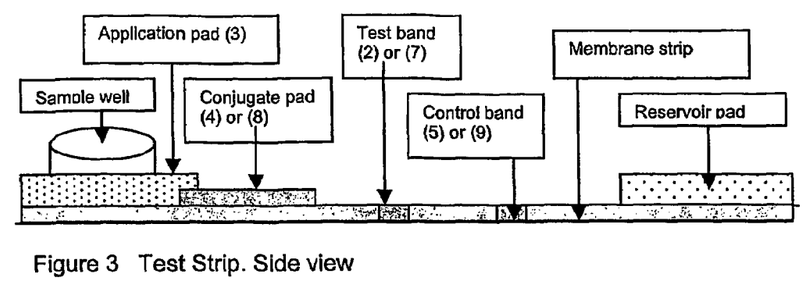
FIG. 3 depicts a side view of the test strips made in accordance with the teachings of the present invention.

The test strip for measuring glycated albumin is shown in FIGS. 1 and 2. The test strip consists of a solid phase support (1), including but not limited to a cellulose nitrate membrane, to which antibody to glycated albumin has been fixed to the solid-phase substrate as a band (2). A sample application pad (3) contacts a conjugate pad (4) containing microparticles coated with anti-glycated albumin antibody. A control band is provided to bind excess unreacted microparticles (5) and a reservoir pad (6) is provided at the distal end of the membrane to absorb excess sample fluid. The test strip is enclosed within a rigid cassette containing a sample well and window segments to allow for visualization and measurement of the test result.

To perform the test a small volume of blood is placed into the sample well. The blood migrates into the sample application pad which filters and binds the red blood cells allowing the plasma to pass through into the conjugate pad where it reacts with the antibody coated microparticles. Any glycated albumin present binds to the anti-glycated albumin antibody-coated microparticles. The microparticles continue to migrate across the cellulose membrane until they come into contact with the fixed band of anti-glycated albumin antibody. Any glycated albumin bound to microparticles becomes bound to the membrane and causes the bound microparticles to form a visible band. The intensity of the band is proportional to the amount of glycated albumin bound to the microparticles. The intensity of the visible band is estimated visually by comparison to a visual standard or measured in an instrument developed for this purpose.

Total Albumin Test

The test strip for measuring total albumin is shown in FIGS. 1 and 2. It consists of a solid phase substrate (1), including but not limited to a cellulose nitrate membrane (1) to which antibody to albumin has been fixed as a band (7). A sample application pad (3) contacts a conjugate pad (8) containing microparticles coated with anti-albumin antibody. A control band (9) is provided to bind excess unreacted microparticles and a reservoir pad (6) is provided at the distal end of the membrane to absorb excess sample fluid. The test strip is enclosed within a rigid cassette containing a sample well and window segments to allow for visualization and measurement of the test result.

To perform the test a small volume of blood is placed into the sample well. The blood migrates from the sample application pad which filters and binds the red blood cells allowing the plasma to pass into the conjugate pad where it reacts with the antibody coated microparticles. Any albumin present binds to the anti-albumin antibody coated microparticles. The microparticles continue to migrate across the cellulose membrane until they come into contact with the fixed band of anti-albumin antibody. Any albumin bound to microparticles becomes bound to the membrane and causes the bound microparticles to form a visible band. The intensity of the band is proportional to the amount of albumin bound to the microparticles. The intensity of the visible band is estimated visually by comparison to a visual standard or measured in an instrument developed for this purpose.

Measuring Instrument

In one embodiment of this invention, the measuring instrument is a reflectance spectrophotometer that is specifically designed to measure the intensity of the glycated albumin test band on the glycated albumin test strip, the total albumin test band on the total albumin test strip, and to calculate a result from these readings. The instrument has two sets of detectors: one detector set is for measuring glycated albumin and the other detector set is for measuring total albumin. The result is then calculated according to a mathematical algorithm derived from data obtained from measurement of standards of glycated and total albumin. The result is expressed as the percent of glycated albumin compared to total albumin present.

Alternatively, other methods for measuring the density of the aggregated microparticles may be employed. For example, in another embodiment of the present invention, the measuring instrument may be a fluorometer that measures the fluorescence that is emitted from microroparticles that have been tagged with a fluorescent dye including, but not limited to, fluorescein or rhodamine red. In this embodiment there will be an excitatory beam of light projected onto the test bands and onto the control bands, and the emitted light from each band will be individually read by the corresponding detectors sensitive to the wavelength of the emitted light. The data reduction and reporting of the result will be as described above for the reflectance spectrophotometer.

EXAMPLE 1

Glycated Albumin Test

A blood sample, such as that obtained from a finger stick, is placed in the sample well and allowed to absorb into the sample application pad. The sample application pad is composed of porous cellulose material but other woven or porous materials including but not limited to glass fibers may be used. The sample application pad has a porosity that does not allow the passage of red blood cells but allows the passage of the plasma. Alternatively, the application pad can be treated with binding agents such as lectins that bind the red blood cells and prevent them from passage through the application membrane.

The filtered plasma sample then flows into a conjugate pad containing microparticles. The conjugate pad is composed of porous cellulose material but other woven or porous materials such as glass fibers may be used. The microparticles are composed of materials including, but not limited to, colloidal gold, latex particles, acrylic particles or polystyrene particles with diameters that may range from approximately 5 nm to 50 nm. Microparticles composed of other materials may also be employed and are within the scope of this invention. In alternative embodiment of the present invention, colored or fluorescent tagged microparticles can be employed to increase the sensitivity of the system.

In embodiments of the present invention, the microparticles are coated with either polyclonal or monoclonal antibodies to glycated albumin. The polyclonal anti-glycated albumin antibodies are prepared in immunized animals, including but not limited to rabbits, sheep, goats, or other immunized species of animals, or by monoclonal antibody techniques. Either the whole antiserum, or the IgG purified fraction, or the affinity purified antibody to glycated albumin may be employed. The methods for immunization of animals and the preparation and purification of antibody is performed according to standard laboratory procedures and are known to those skilled in the art.

Similarly, the methods of developing monoclonal antibodies is performed according to standard laboratory procedures and are known to those skilled in the art. The microparticles may be coated with the antibody by passive adsorption, by chemical conjugation such as covalent binding, or through binding to an intermediate agent such as to Protein A-coated microparticles. The methods for coating microparticles are performed according to standard laboratory procedures and are familiar to those skilled in the art.

When the test sample comes into contact with the antibody coated microparticles, the antibody will bind any glycated albumin present. The microparticles will continue to migrate across the membrane until they reach the band of anti-glycated albumin antibody fixed to the membrane. Any microparticles containing bound glycated albumin will become bound to the fixed band of anti-glycated albumin antibody to form a visible band.

Alternatively the membrane may be treated with chemicals known to bind glycated proteins such as phenyl boronic acids which are applied as a band to the membrane strip. Any microparticles containing bound glycated albumin will become bound to the fixed band of phenyl boronic acid to form a visible band. Independent of the method by which the glycated albumin becomes bound to the test strip, the density of the band formed will be directly proportional to the amount of glycated albumin present in the blood sample. The density of the band can be measured using a reflectance spectrometer for colored microparticles or a fluorometer for microparicles tagged with a fluorescent compound. The measurements are used to calculate the percentage of glycated albumin compared to total albumin in the blood sample.

In order to verify that the test strips are functioning correctly each test strip can additionally have a control band located distal to the test band. For the glycated albumin test strip this control band is composed of antibody directed against the species antibody that was used to coat the microparticles. For example, if rabbit anti-human glycated albumin antibody used to coat the microparticles, then the control band would use another species such as goat or sheep antibodies directed against rabbit IgG immunoglobulin. The antibodies in the control band bind to the excess unreacted antibody-coated microparticles that were not bound to the test band but continued to migrate across the membrane until bound by the control reagent. The intensity of the control band is measured using a reflectance spectrometer or fluorometer and the data is used to determine if the test is performing correctly.

EXAMPLE 2

Total Albumin Test

A blood sample, such as that obtained from a finger stick, is placed in the sample well and allowed to absorb into the sample application pad. The sample application pad is composed of porous cellulose material but other woven or porous materials, including but not limited to glass fibers may be used. The sample application has a porosity that does not allow the passage of red blood cells but allows the passage of the plasma. Alternatively, the application pad can be treated with binding agents such as lectins that bind the red blood cells and prevent them from passage through the application membrane.

The filtered plasma sample then flows into a conjugate pad containing microparticles. The conjugate pad is composed of porous cellulose material but other woven or porous materials, including but not limited to glass fibers may be used. The microparticles are composed of materials including, but not limited to, colloidal gold, latex particles, acrylic particles or polystyrene particles with diameters that may range from approximately 5 nm to 50 nm. Microparticles composed of other materials may also be employed and are within the scope of this invention. Colored or fluorescence tagged microparticles may be employed to increase the sensitivity of measurement of the result.

In embodiments of the present invention, the microparticles are coated with either polyclonal or monoclonal antibodies to glycated albumin. The polyclonal anti-albumin antibodies are prepared in immunized animals including but not limited to rabbits, sheep, goats, or other immunized species of animals, or by monoclonal antibody techniques. Either the whole antiserum, or the IgG purified fraction, or the affinity purified antibody to albumin may be employed. The methods for immunization of animals and the preparation and purification of antibody is performed according to standard laboratory procedures and are known to those skilled in the art. Similarly, the methods of developing monoclonal antibodies are performed according to standard laboratory procedures and are known to those skilled in the art.

The microparticles may be coated with the antibody by passive adsorption, by chemical conjugation such as covalent binding, or through binding to an intermediate agent such as to Protein A-coated microparticles. The methods for coating microparticles are performed according to standard laboratory procedures and are familiar to those skilled in the art.

When the test sample comes into contact with the antibody coated microparticles the antibody binds any albumin present. The microparticles continue to migrate across the membrane until they reach the band of anti-albumin antibody fixed to the membrane. Any microparticles containing bound albumin become bound to the fixed band of anti-albumin antibody to form a visible band. The density of the band formed is directly proportional to the amount of albumin present in the blood sample. The density of the band is measured using a reflectance spectrometer for colored microparticles or a fluorometer for microparticles tagged with a fluorescent compound. The measurements are used to calculate the percentage of glycated albumin compared to total albumin in the blood sample.

In order to verify that the test strips are functioning correctly each test strip has an additional band of fixed reagent located distal to the test band. For the test strip, this control band is composed of antibody directed against the species antibody that was used to coat the microparticles. For example, if rabbit anti-human albumin antibody was used to coat the microparticles then the control band uses another species such as goat or sheep antibodies directed against rabbit IgG immunoglobulin. The antibodies in the control band bind to the excess unreacted antibody coated microparticles that were not bound to the test band but continued to migrate across the membrane until bound by the control reagent. The intensity of the control band is measured using a reflectance spectrometer or fluorometer and the data is used to determine if the test is performing correctly.

EXAMPLE 3

The Measuring Instrument

Figure 4:
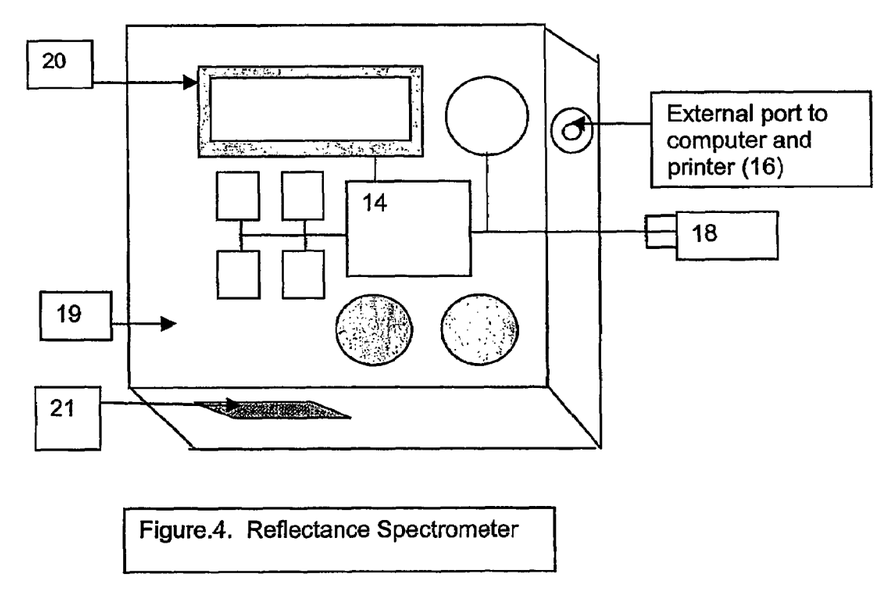
FIG. 4 depicts a reflectance spectrometer as used with the test strips made in accordance with the methods of the present invention.

The measuring instrument shown in FIG. 4a is a reflectance spectrometer and is composed of the following components: A detector (10) calibrated to read the reflectance of the microparticles fixed to the glycated albumin band on the glycated albumin test strip; a detector (11) calibrated to read the reflectance of the microparticles fixed to the control band on the glycated albumin test strip; a detector (12) calibrated to read the reflectance of the microparticles fixed to the total albumin band on the total albumin test strip; a detector (13) calibrated to read the reflectance of the microparticles fixed to the control band on the total albumin test strip; a computing chip and electronic circuitry (14) to collect the data from the detectors and to calculate the result.

The calculations are based on a mathematical algorithm and a reference standard curve. The standard curve is derived from value assigned standards and the instrument is precalibrated at the manufacturing facility before it is distributed. The result is expressed as the percent of glycated albumin compared to total albumin and displayed on a liquid crystal display (15). Successive results obtained over a period of time are stored in the instrument and can be retrieved on demand and displayed in numerical format or in graphical format. Typically, the result will be displayed along with the date of the test. The user may then select to have all the previous stored test results and their date displayed, or have all the results presented as a graph so that any trends can be identified. In order to enter commands to the internal computer the instrument may contain either buttons or a keyboard on its exterior case.

The results can also be downloaded via an external port to an external computer and/or printed on an external printer (16). The instrument's electronics are powered by an internal battery (17) and/or external power source (18). The components are housed in a rigid exterior case (19) with a window (20) for the display monitor and an aperture (21) for inserting the test cassette.

Alternatively, the measuring instrument may be a fluorometer (FIG. 4b) that measures the density of aggregated microparticles that have been tagged with a fluorescent dye such fluorescein or rhodamine. The fluorometer is composed of the following components: A detector (22) calibrated to read the fluorescence of the microparticles fixed to the glycated albumin band on the glycated albumin test strip; a detector (23) calibrated to read the fluorescence of the microparticles fixed to the control band on the glycated albumin test strip; a detector (24) calibrated to read the fluorescence of the microparticles fixed to the total albumin band on the total albumin test strip; a detector (25) calibrated to read the fluorescence of the microparticles fixed to the control band on the total albumin test strip; a computing chip and electronic circuitry (26) to collect the data from the detectors and to calculate the result. Using fluorescein tagged microparticles as an example, the excitatory beam of light (492 nm wavelength) is projected onto the test bands and onto the control bands, and the emitted light from each band is individually read by the corresponding detectors sensitive to the wavelength (518 nm) of the emitted light. Alternatively, other fluorescent compounds may be used and the wavelength of the exciting beam and the wavelength of the resulting fluorescence to be measured is adjusted accordingly.

Figure 4B:
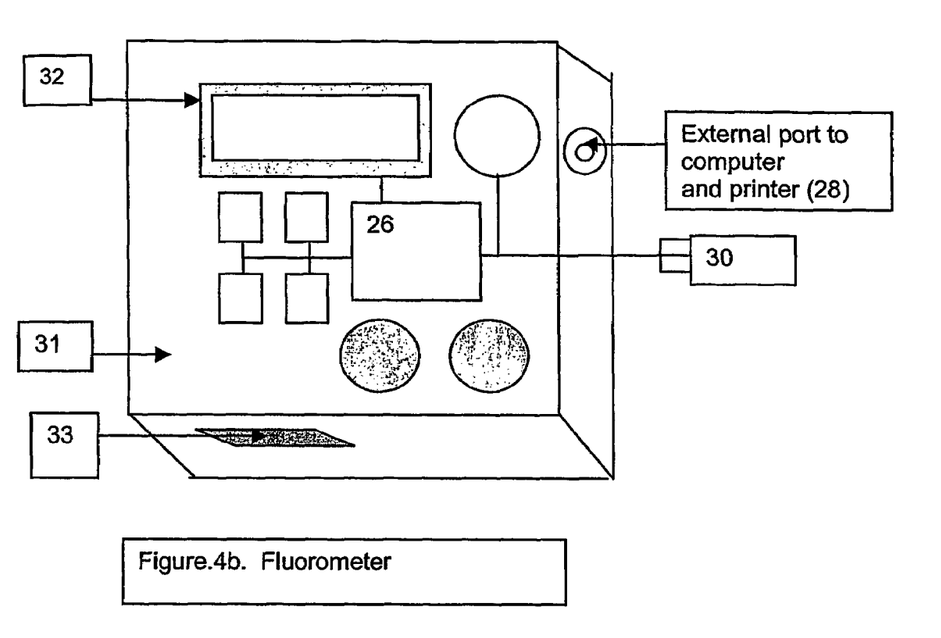
FIG. 4b depicts a fluorometer as used with the test strips made in accordance with the methods of the present invention.

The calculations are based on a mathematical algorithm and a reference standard curve. The standard curve is derived from value assigned standards and the instrument is precalibrated at the manufacturing facility before distribution. The result is expressed as the percent of glycated albumin compared to total albumin and is displayed on a liquid crystal display (27). Successive results obtained over a period of time are stored in the instrument and can be retrieved on demand and displayed in numerical format or in graphical format. Typically, the result is displayed along with the date of the test. The user may then select to have all the previous stored test results and their date displayed, or have all the results presented as a graph so that any trends can be identified. In order to enter commands to the internal computer the instrument may contain either buttons or a keyboard on its exterior case.

The results can also be downloaded via an external port to an external computer and/or printed on an external printer (28). The instrument's electronics are powered by an internal battery (29) and/or external power source (30). The components are housed in a rigid exterior case (31) with a window (32) for the display monitor and an aperture (33) for inserting the test cassette.

Figure 5:
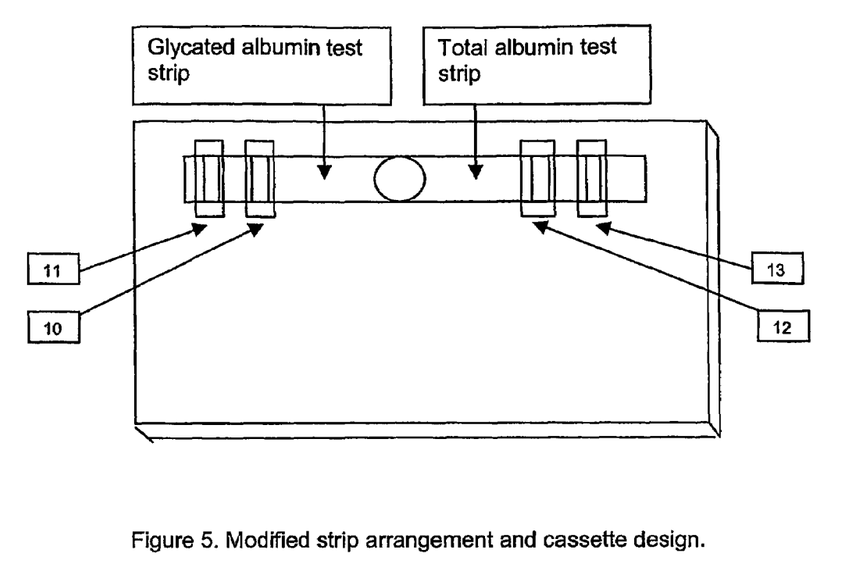
FIG. 5 depicts a first view of a test strip cassette made in accordance with the teachings of the present invention.
Figure 6:
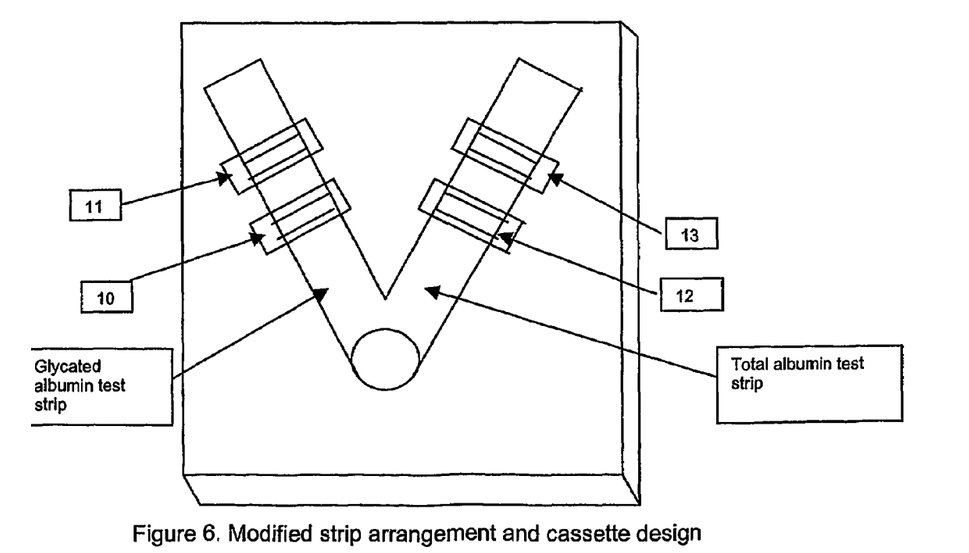
FIG. 6 depicts a second view of a test strip cassette made in accordance with the teachings of the present invention.

In one embodiment of this invention, the test cassette is designed to enclose two test strips arranged in a parallel fashion (FIG. 1) and the sample application well is constructed so that the test sample fluid can migrate across both test strips simultaneously. However, other test cassette configurations may be employed using the same principles described in this invention and are considered to be within the scope of this invention. For example, the sample application well may be centrally located with the glycated albumin test strip and the total albumin test strip pointing outward in a radial direction. FIG. 5 shows the test strips arrangement as diametrically opposite to each other and FIG. 6 shows the test strips to be at an angle to each other. In these examples the test cassette is in the shape of a rectangular or square configuration. The aperture in the measuring instrument for inserting these cassettes is adjusted to accommodate the shape of these cassettes.

In an embodiment of the present invention, the measuring instrument is a reflectance spectrometer which measures a particular wavelength of the light reflected from the colored microparticles. The amount of reflected light measured at the test band and control band sites is directly proportional to the density of the aggregated microparticles at each site Alternatively, a fluorometer may be used as the measuring instrument. In this example, the microparticles are tagged with an internal fluorescent dye such as fluorescein or rhodamine red. The fluorescence-tagged microparticles are excited at one wavelength of light which causes them to fluoresce at a different wavelength of light. The amount of fluorescence measured at the test band and control band sites is directly proportional to the density of the aggregated microparticles at each site.

In another embodiment of the present invention, the measuring instrument is of small size, compact and lightweight. In general, it is similar in appearance and design to the various handheld glucometers in common usage. Such variations are cosmetic in nature and are considered to be within the scope of this invention.

What is claimed is:

1. A system for detecting glycated albumin in a sample and determining the percent glycated albumin comprising:
    a solid support comprising a lateral flow membrane;
    a single application pad containing a sample well disposed on said solid support, wherein said application pad comprises a porous material to retain red blood cells from said sample in said application pad;
    a first assay comprising a first test strip the measures glycated albumin in said sample wherein said first test strip comprises sequential bands wherein one of said bands is a first control band;
    a second assay comprising a second test strip that measures total albumin in the same sample as said first assay wherein said test strip comprises sequential bands wherein one of said bands is a second control band; and
    means for calculating percent glycated albumin,
    wherein said first test strip has disposed therein microparticles which specifically bind glycated albumin in said sample and said second test strip has disposed therein microparticles which specifically bind total albumin in said sample.

2. The system of claim 1 wherein said system is an immunochromatographic system.

3. The system of claim 1 wherein said
    means for calculating percent glycated albumin comprises
        a measurement device that reads, calculates and displays the result as the percentage of glycated albumin compared to total albumin in the sample.

4. The system of claim 3 wherein said measurement device is a reflectance spectrometer or a fluorometer comprising:
    a detector for measuring the glycated albumin test result;
    a detector for measuring the glycated albumin control band;
    a detector for measuring the total albumin test result;
    a detector for measuring the total albumin control band;
    an internal computer chip for measurement and calculation;
    a liquid crystal display;
    an external port to transfer data to an external computer and/or printer;
    a battery and/or an external power source; and
    a rigid external case with an aperture for inserting the test cassette.

5. The system of claim 4 whereby the one or more than one test result can by displayed on said measurement device's liquid crystal display in numerical format or in graphical format.

6. The system of claim 4 further comprising an internal memory chip capable of storing one or more than one test result.

7. The system of claim 6 whereby the one or more than one test result can be transferred to an external computer or printer.

8. The system of claim 1, wherein said first test strip has disposed therein bands comprising:
    a first conjugate band comprising microparticles coated with a first antibody to glycated albumin,
    a first test band comprising a glycated albumin-specific immobilization agent covalently bound to said test strip; and
    a first control band.

9. The system of claim 8 wherein said immobilization agent is an antibody to glycated albumin.

10. The system of claim 8 wherein said microparticles are selected from the group consisting of colloidal gold particles, latex particles, polystyrene particles, acrylic particles or other solid phase microparticles.

11. The system of claim 1 wherein said second test strip has disposed therein bands comprising:
    a second conjugate band comprising microparticles coated with a first antibody to albumin,
    a second test band comprising a second antibody to albumin covalently bound to said second test strip; and
    a second control band.

12. The system of claim 11 wherein said microparticles are selected from the group consisting of colloidal gold particles, latex particles, polystyrene particles, acrylic particles or other solid phase microparticles.

13. The system of either of claims 10 or 12, wherein said microparticles are colored or tagged with a fluorescent compound.

14. The system of claim 1 wherein the first test strip and the second test strip are arranged in configuration selected from the group consisting of parallel, opposite to each other, and at an angle to each other.

15. The system of claim 1 wherein the first test strip and the second test strip are enclosed in a rigid cassette.

16. A method of monitoring glycated albumin and determining a percent glycated albumin level comprising:
   depositing a drop of blood into a sample well of an immunochromatography system test cassette according to claim 1;
   transferring said blood into the sample application pad thereby allowing blood plasma to pass into a first conjugate band of a first test strip and into a second conjugate band of a second test strip;
   binding glycated albumin in said blood plasma to anti-glycated albumin antibody-coated microparticles in said first conjugate band;
   binding albumin in said blood plasma to anti-total albumin antibody-coated microparticles in said second first conjugate band;
   allowing glycated albumin and albumin bound antibody-coated microparticles in each of said first test strip and said second test strip to individually migrate across said conjugate bands to fixed bands of membrane-bound antibody;
   binding said glycated albumin and albumin-bound antibody-coated microparticles in each of said first test strip and said second test strip to said membrane-bound antibodies to form colored or fluorescent bands;
   allowing unbound antibody-coated microparticles to pass into a first control band in said first test strip and a second control band in said second test strip;
   inserting said immunochromatography system test cassette into a measurement device;
   providing numerical results of glycated albumin levels from said first test strip and total albumin levels from said second test strip; and
   calculating said percent glycated albumin.

* * * * *